(12) United States Patent
Allen

(10) Patent No.: US 7,614,276 B2
(45) Date of Patent: Nov. 10, 2009

(54) METHOD FOR DETERMINING ABSOLUTE DENSITY OF CEMENT SLURRY

(76) Inventor: Thomas E. Allen, 9722 S. Oswego, Tulsa, OK (US) 74137

( * ) Notice: Subject to any disclaimer, the term of this patent is extended or adjusted under 35 U.S.C. 154(b) by 322 days.

(21) Appl. No.: 11/516,540

(22) Filed: Sep. 6, 2006

(65) Prior Publication Data
US 2008/0053220 A1 Mar. 6, 2008

(51) Int. Cl.
*G01N 9/00* (2006.01)
(52) U.S. Cl. ...................................... 73/32 R
(58) Field of Classification Search ............. 73/32 R, 73/438, 433, 32 A
See application file for complete search history.

(56) References Cited

U.S. PATENT DOCUMENTS

| | | | |
|---|---|---|---|
| 4,779,186 | A | 10/1988 | Handke et al. |
| 5,027,267 | A | 6/1991 | Pitts et al. |
| 5,114,239 | A | 5/1992 | Allen |
| 5,281,023 | A | 1/1994 | Cedillo et al. |
| 5,590,958 | A | 1/1997 | Dearing, Sr. et al. |
| 5,624,182 | A | 4/1997 | Dearing, Sr. et al. |
| 5,775,803 | A | 7/1998 | Montgomery et al. |
| 6,332,111 | B1 | 12/2001 | Fincke |
| 6,598,457 | B2 | 7/2003 | Sullivan et al. |
| 7,117,717 | B2 | 10/2006 | Mattar et al. |
| 2005/0138993 | A1 | 6/2005 | Mattar et al. |
| 2008/0053221 | A1* | 3/2008 | Allen .................... 73/32 R |

OTHER PUBLICATIONS

S.K. Nickles, Halliburton Services, An Instrument for Measuring the Density of Air Entrained Fluids, Society of Petroleum Engineers of AIME, Paner No. SPE 4092 Ca. 1972.

* cited by examiner

*Primary Examiner*—Hezron Williams
*Assistant Examiner*—Gunnar J Gissel

(57) ABSTRACT

A method for determining absolute density of a slurry that typically contains entrained air, such as cement slurry, in a continuous mixing operation such those used in cementing a gas or oil well. The method obtains density measurements of a slurry at two different pressures and then uses the two density measurements and the two pressure measurements to compute absolute density of the slurry employing the following formula at isothermal conditions: $Dabs=D1/(1-((D1/D2-1)/(P1/P2-1)))$, where $Dabs$=absolute density, $D1$=first density, $D2$=second density, $P1$=absolute pressure at which the first density was measured, and $P2$=absolute pressure at which the second density was measured.

16 Claims, 3 Drawing Sheets

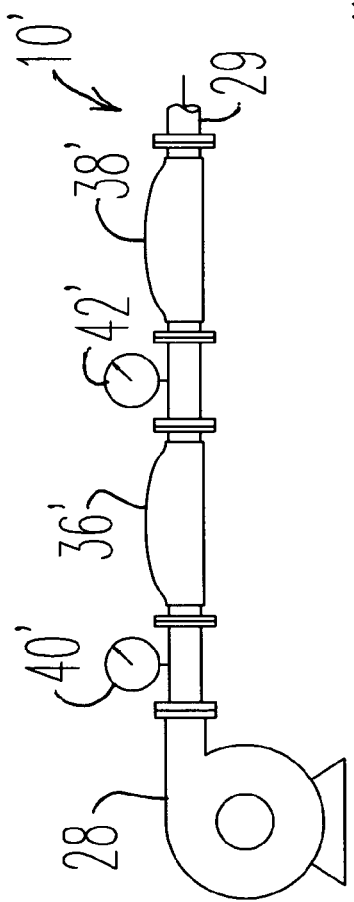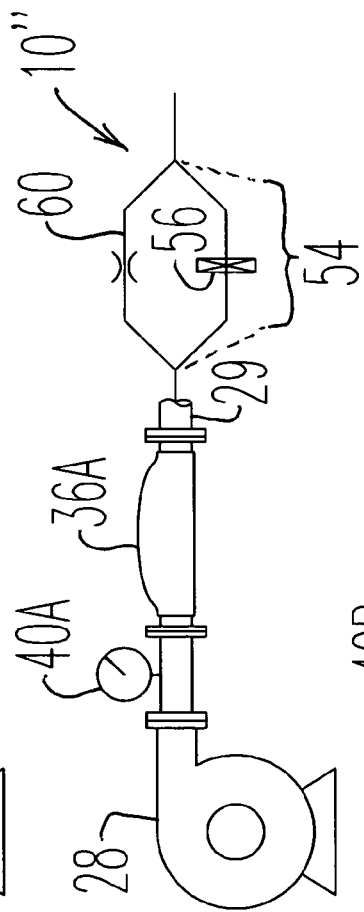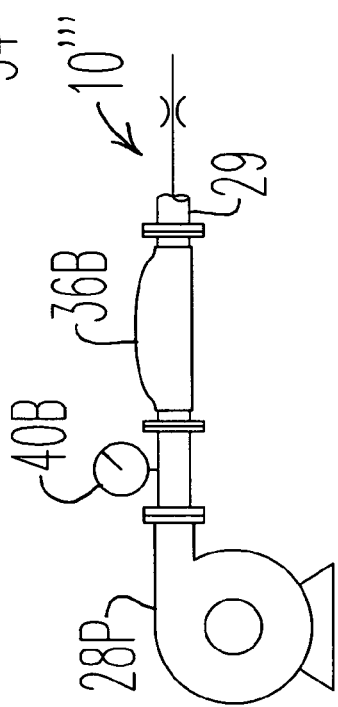

METHOD FOR DETERMINING ABSOLUTE DENSITY OF CEMENT SLURRY

BACKGROUND OF THE INVENTION

1. Field of the Invention

The present invention relates to a method for determining absolute density of a fluid, such as cement slurry, that typically contains entrained air. The term absolute density as used herein refers to the density of a fluid containing entrained air that would be theoretically obtained when measured at infinite pressure as if the entrained air was not present in the fluid. This method involves taking density measurements of the slurry at two different pressures and using these measurements to compute the absolute density of the slurry. This method is particularly designed to provide the operator with almost instantaneous readings of absolute density that can then be used to control the production of the slurry to produce slurry of the desired air free density in a continuous slurry mixing operation, such as cement slurry needed in cementing an oil or gas well.

2. Description of the Related Art

All cement slurry has some air entrainment. The problem with air entrainment is that it affects the density measurement while mixing the slurry. Current technology densitometers can determine the slurry density accurately. The problem with this measurement is that the measurement includes the air that is in the slurry. After the slurry is pumped into the well, the pressure on the slurry becomes very high, maybe several thousand psi. This high pressure causes the entrained air to be compressed such that it no longer creates a void volume in the slurry. Thus, slurry that has entrained air at atmospheric pressure will have a density greater downhole than when it is measured at the surface.

This difference in slurry measurement can cause problems with completion of the cementing job because of the higher hydrostatic pressure at the bottom of the well due to the density difference and because of the higher viscosity of the slurry. The higher viscosity causes a higher fiction pressure while pumping the slurry. This adds to the higher hydrostatic pressure to give a higher downhole pumping pressure. The higher pressure can cause loss of circulation and possible failure of the job.

This density measurement problem is further complicated by the fact that cement slurry contains three components: water, air, and a fixed dry blend of cement and additives that has an average absolute density. If cement slurry were composed of only two components, such as air and a liquid, the amount of entrained gases in that liquid mixture could be measured by methods such as the one taught in U.S. Pat. No. 6,598,457 which teaches a method for measuring entrained air in a two component, i.e. air and liquid, sample. However, because cement slurry contains three components, it presents problems in that both the amount of water and the amount of air can alter the apparent slurry density. By measuring density alone, the actual dry blend of cement and additives verses water ratio is not known since both water and air can cause the density to be altered. As an example, a first slurry with a measured density which is measured at low or atmospheric pressure may have exactly the correct cement to water ratio. However, a second slurry may have the same density as the first one, but because the second one contains a different amount of entrained air, the second slurry will have a ratio of dry blend of cement and additives verses water that will be in error.

Three ways have been and are currently being used to solve this problem. The first way is to use a high pressure downhole densitometer on the downstream side of the high pressure pumps that are used to pump slurry downhole. The second way is to use a pressurized mud cup measuring instrument. The third way is to use an average offset.

The first way is to use a high pressure downhole densitometer on the downstream side of the high pressure pumps that are used to pump slurry downhole. This point of measurement usually has a high enough pressure to eliminate most the effects of air entrainment on density measurement. However, a densitometer that is capable of measurement at high pressure employs a radioactive source. Measurement with this device is limited in accuracy, requires frequent calibration, and has a slow response time. In addition, this type device is undesirable due to the regulatory requirements associated with using a radioactive device. Also, this point of measurement is far enough downstream of the mixing system that its measured value could not be used for continuous control purposes because of further time delay.

The second way is to use a pressurized mud cup. This method is described in the 1972 Society of Petroleum Engineers of AIME Paper Number SPE 4092 entitled An Instrument for Measuring the Density of Air Entrained Fluids authored by S. K. Nickles of Halliburton Services. The pressurized mud cup is a device that requires a sample of the slurry from the mixing tub and then uses that sample to determine the density of the slurry under pressure. The accuracy of this device is limited to the skill of the operator. In addition, this is not a continuous measurement device. It takes a minimum of 3 minutes to take the sample and make the measurement. Thus, this device is not suitable for use for continuous density control. It can only be used as a spot check on the system density.

The third way is to use an average offset. Commonly, density is measured with radioactive or non-radioactive devices in the recirculation line of the mixing system. Since it is known that the slurry will always have some air entrainment, the operator will typically use an estimated average offset to compensate for the air entrainment. The amount of offset may be a guess or can be better estimated by comparing the circulating density measurement with the measurement produced by the pressurized mud cup testing described above. However, even if this estimate is determined from the pressurized mud cup measurement, it is not real time and slurry mixing conditions are constantly changing in a well cementing operation.

The present invention addresses the shortcomings of the prior methods by providing a new solution to this density measurement problem. This new solution obtains density measurements of a slurry at two different pressures and then uses the two density measurements and the two pressure measurements to compute absolute density of the slurry employing the following formula.

$$D_{abs} = D1/(1-((D1/D2-1)/((P1/P2)^{1/n}-1)))$$

Where:
$D_{abs}$=absolute density
$D1$=first density
$D2$=second density
$P1$=absolute pressure at which the first density was measured
$P2$=absolute pressure at which the second density was measured
$n$=exponent for pressure-volume polytropic process relationship, $P1 \times V1^n = P2 \times V2^n$ The fluid slurry passing through the densitometers illustrated in FIGS. 1-4 can be characterized as an isothermal process where the entrained air is expanded and compressed at a near constant temperature. For an isothermal process, "n" can be assumed to be equal to 1.0 for air compression up to several hundred psi. With this assumption, the formula for Dabs becomes simplified to:

$$Dabs=D1/(1-((D1/D2-1)/(P1/P2-1)))$$

The calculation employs the ideal gas model for an isothermal or constant temperature process to determine the behavior of entrained gas in a liquid or slurry. Also, for the purposes of this discussion, absolute pressure refers to the pressure measured relative to absolute zero pressure or the pressure that would occur at absolute vacuum. Absolute pressure is the sum of gauge pressure and atmospheric pressure.

For other fluids containing entrained gas where a value of "n"=1.0 is not adequate for accurate calculations, the following procedure can be used to experimentally determine "n". "Lay off successive values of P & V, measured at chosen points on the curve under investigation, on logarithmic cross-section paper; or, lay off values of log P and Log V on ordinary cross-section paper. If "n" is a constant, the points will lie in a straight line, and the slope of the line gives the value of n. If two representative points P1, V1 and P2, V2 be chosen, then n=(log P1−log P2)/(log V2−log V1). Several pairs of points should be used to test the constancy of n." This procedure was taken from the Ref. *Mechanical Engineers Handbook*, Sixth Edition, McGraw-Hill Book Company, Inc. More complex mathematical models can be developed for curve fitting experimental data for "n".

SUMMARY OF THE INVENTION

The present invention is a new method for determining absolute density of a slurry, such as cement slurry, in a continuous mixing operation such as those used in cementing a gas or oil well. The present invention relates to a method for determining absolute density of slurry, such as cement slurry, that typically contains entrained air. This new solution obtains density measurements of a slurry at two different pressures and then uses the two density measurements and the two pressure measurements to compute absolute density of the slurry employing the following formula.

$$Dabs=D1/(1-((D1/D2-1)/((P1/P2)^{1/n}1)))$$

Where:
Dabs=absolute density
D1=first density
D2=second density
P1=absolute pressure at which the first density was measured
P2=absolute pressure at which the second density was measured
n=exponent for pressure-volume polytropic process relationship, $P1 \times V1^n = P2 \times V2^n$ For an isothermal process, where "n" can be assumed to be equal to 1.0, the formula is simplified to the following:

$$Dabs=D1/(1-((D1/D2-1)/(P1/P2-1)))$$

In a first equipment arrangement for the present invention, two densitometers are used in a system along with two corresponding pressure transducers. This first arrangement of equipment requires that the two densitometers be installed in a way that they draw from the same slurry source but operate at different pressures. Typically, the first densitometer is installed in the recirculation line going to the cement slurry mixer and the second densitometer is installed in the line that delivers slurry to the downhole pump suction. This two pump arrangement is very typical, regardless of whether or not density is being measured.

In a second equipment arrangement for the present invention, two densitometers are installed in series along with the corresponding pressure transducers. Both densitometers, for practical purposes, are measuring the same fluid which is passing by each densitometer milli-seconds apart but at different pressures. The second densitometer is operating at a lower pressure by virtue of the pressure drop in the first densitometer.

Both third and fourth equipment arrangements for the present invention would use only one densitometer, one pressure transducer and a method of cycling by intermittently or continuously changing the pressure within the densitometer. Both of these two equipment arrangements measure the maximum and minimum pressures and corresponding densities during the cycle and use those measurements to compute absolute density. The third equipment arrangement intermittently or continuously changes the pressure within the densitometer by use of a downstream manifold with one valve that would be opened and closed in a manner that the pressure is changed intermittently or changed to create a sinusoidal pressure in the densitometer.

The fourth equipment arrangement continuously changes the pressure within the densitometer by using a pulsing pump, such as an air diaphragm pump, for supplying the flow to the densitometer.

BRIEF DESCRIPTION OF THE DRAWINGS

FIG. 2 is a schematic diagram showing a second equipment arrangement for the present invention.

FIG. 3 is a schematic diagram showing a third equipment arrangement for the present invention.

FIG. 4 is a schematic diagram showing a fourth equipment arrangement for the present invention.

DETAILED DESCRIPTION OF THE PREFERRED EMBODIMENT

The present invention is a method for determining absolute density of a slurry, such as cement slurry, in a continuous mixing operation such as used in cementing a gas or oil well. The present invention relates to a method for determining absolute density of slurry, such as cement slurry, that typically contains entrained air. The present method obtains density measurements D1 and D2 of a slurry at two different pressures P1 and P2 and then uses the two density measurements D1 and D2 and the two pressure measurements P1 and P2 to compute absolute density Dabs of the slurry employing the following formula.

$$Dabs=D1/(1-((D1/D2-1)/((P1/P2)^{1/n}-1)))$$

Where:
Dabs=absolute density
D1=first density

D2=second density
P1=absolute pressure at which the first density was measured
P2=absolute pressure at which the second density was measured
n=exponent for pressure-volume polytropic process relationship, $P1 \times V1^n = P2 \times V2^n$ The fluid slurry passing through the densitometers illustrated in FIGS. 1-4 can be characterized as an isothermal process where the entrained air is expanded and compressed at a near constant temperature. For an isothermal process, "n" can be assumed to be equal to 1.0 for air compression up to several hundred psi. With this assumption, the formula for Dabs becomes simplified to the following:

$$Dabs = D1/(1-((D1/D2-1)/(P1/P2-1)))$$

In performing this calculation, the first density and the second density measurements can be interchanged in the calculation so long as the first pressure and the second pressure measurements are likewise interchanged. Stated another way, it is not critical to the calculation that a particular density measurement and associated pressure measurement be entered into the calculation as P1 and D1 so long as the pressure measurement and its associated density measurement are jointly designated as either P1 and D1 or jointly as P2 and D2 instead of as P1 and D2 or as P2 and D1.

Figure 1:
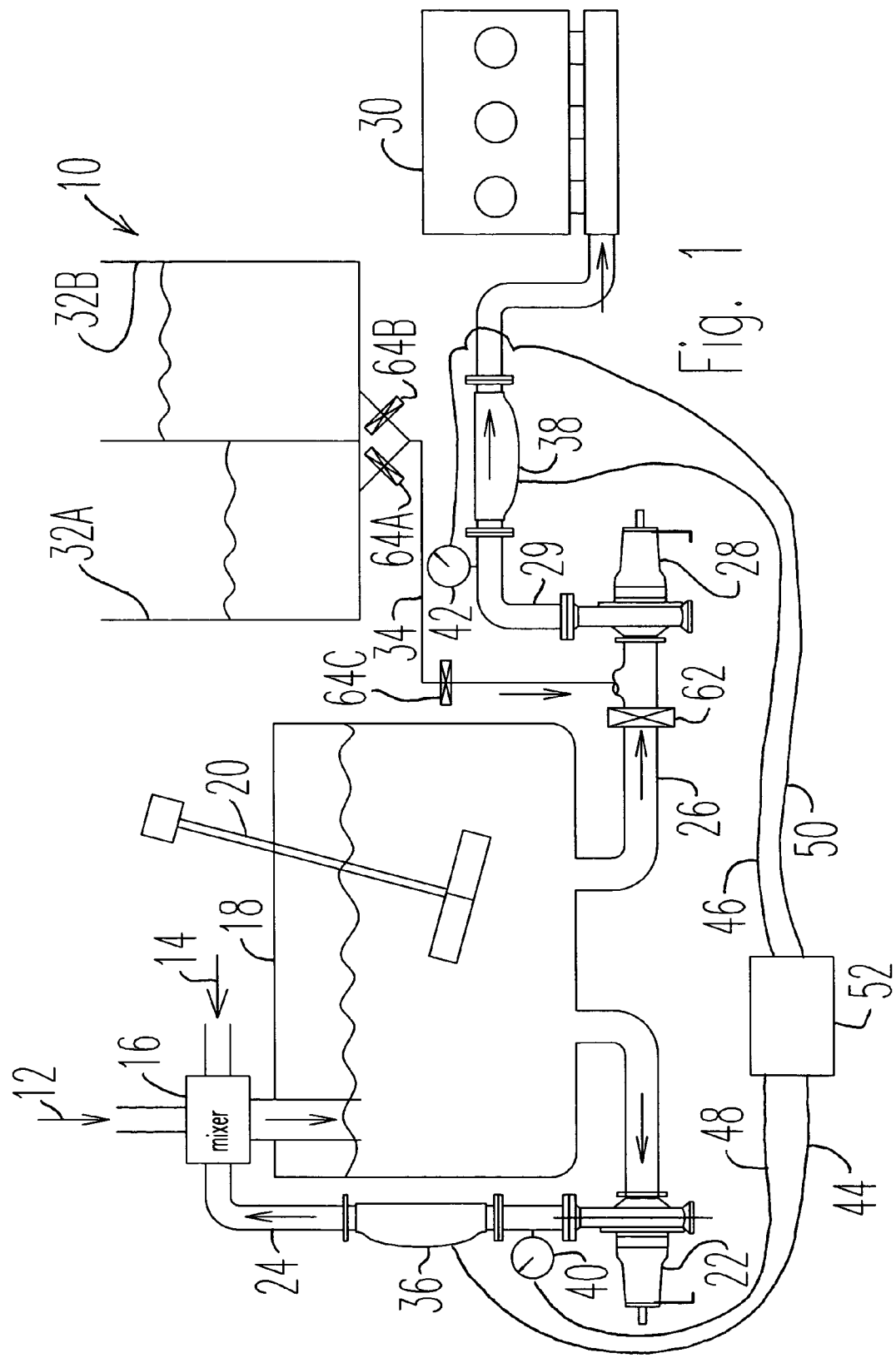
FIG. 1 is a schematic diagram showing a first equipment arrangement used to practice the present invention in association with well cementing equipment.

Referring now to the drawings and initially to FIG. 1, there is illustrated a first equipment arrangement 10 used to practice the present invention in association with well cementing equipment. In a well cementing operation, bulk cement 12 is mixed with water 14 in a cement slurry mixer 16 which feeds the slurry mixture to a slurry tank 18. The slurry tank 18 is provided with a stirrer 20 to keep the slurry mixed and also provided with a centrifugal recirculation pump 22 that recirculates the slurry from the slurry tank 18 to the cement slurry mixer 16 via a recirculation line 24. An upsteam transfer line 26 also feeds slurry from the slurry tank 18 to a centrifugal transfer pump 28 which pumps the slurry to the downhole pump 30 via a downstream transfer line 29. Displacement tanks 32A and 32B are connected to the transfer line 26 via a displacement line 34 to feed displacement fluid to the downhole pump 30 during the displacement phase of well cementing.

As shown in FIG. 1, typically a first densitometer 36 is provided in the recirculation line 24 and a second densitometer 38 is provided in the downstream transfer line 29 downstream of where the displacement line 34 feeds into the upstream transfer line 26. The present invention adds a pressure meter 40 and 42 at each of the two densitometers 36 and 38, respectively, thereby allowing measurement of pressure P1 and P2 corresponding to density D1 and D2 at the same time at each of the two densitometers 36 and 38.

In a first equipment arrangement for the present invention, two densitometers 36 and 38, such as Micro Motion D300 or F300 (accuracy of +/−0.001 specific gravity), are used in a system along with two corresponding pressure transducers 40 and 42. This first arrangement of equipment requires that the two densitometers 36 and 38 be installed in a way that they draw from the same slurry source but operate at different pressures. As illustrated, each of the densitometers 36 and 38 and each of the pressure transducers 40 and 42 provide continuous density and pressure measurements D1, D2, P2 and P2 via electronic feeds 44, 46, 48 and 50 to a computer 52 that calculates absolute density for the slurry continually. Alternately, measured values can be manually recorded and the absolute density manually calculated. Although not illustrated, the computer 52 would normally be utilized to control the equipment that supplies bulk cement 12 and water 14 to the cement slurry mixer 16 for the cement mixing operation in order to achieve the proper density of slurry.

This arrangement of two densitometers 36 and 38 is sometimes used today but corresponding pressures P1 and P2 are usually not measured and absolute density Dabs has not been calculated from these two sets of density and pressure measurements D1, D2, P1 and P2. Typically, the first densitometer 36 is installed in the recirculation line 24 going to the cement slurry mixer 16 and the second densitometer 38 is installed in the downstream transfer line 29 that delivers slurry to suction of the downhole pump 30. This two pump arrangement is very typical, regardless of whether or not density is being measured.

Referring now to FIG. 2, a second equipment arrangement 10' for the present invention is illustrated. This second equipment arrangement 10' employs first alternate first and second densitometers 36' and 38' that are installed in series along with the corresponding first alternate first and second pressure transducers 40' and 42'. These first alternate densitometers 36' and 38' would typically be installed either in the recirculation line 24 or in the downstream transfer line 29 downstream of the transfer pump 28 and downstream of where the displacement line 34 feeds into the upsteam transfer line 26. Both first alternate densitometers 36' and 38', for practical purposes, are measuring the same fluid which is passing by each first alternate densitometer 36' and 38' milliseconds apart but at different pressures P1 and P2. The first alternate second densitometer 38' is operating at a lower pressure P2 than the first alternate first densitometer 36' by virtue of the pressure drop in the first alternate first densitometer 36'.

Both the first and second equipment arrangements 10 and 10' can be used to calculate absolute density Dabs. However, the first arrangement 10 would work even if the fluid was not moving, as long as the fluid in both densitometers 36 and 38 is representative and the densitometers 36 and 38 are under different pressures P1 and P2. For a practical matter during cementing operations, both densitometers 36 and 38 will have a measurable flow going through them.

The second equipment arrangement 10' requires that the fluid be moving at such a rate that a measurable pressure drop takes place in the first alternate densitometers 36' and 38'. However, no matter which arrangement is being used, the determination of absolute density Dabs for cementing services will greatly improve the quality and success rate of cementing operations.

Both the second equipment arrangement 10' and the third equipment arrangement 10" employ different methods of downstream restriction in order to produce two different pressures P1 and P2. The second equipment arrangement 10' employs the first alternate second densitometer 38' as the flow restricting mechanism, and the third equipment arrangement 10 employs a variable restriction in the form of a downstream manifold 54 provided downstream of a single second alternate densitometer 36A to produce varying back pressure at the single densitometer 36A, as will be more fully explained hereafter.

As illustrated in FIG. 3, the third equipment arrangement 10" for the present invention would use only one second alternate densitometer 36A and one second alternate pressure transducer 40A and a method of varying intermittently or continuously changing the pressure within the second alternate densitometer 36A. Likewise, as illustrated in FIG. 4, the fourth equipment arrangement 10''' for the present invention would use only one third alternate densitometer 36B and one third alternate pressure transducer 40B and a method of varying intermittently or continuously changing flow through the third alternate densitometer 36B, and therefore, the pressure within the third alternate densitometer 36B. The second and third alternate densitometer 36A and 36B employed in these two equipment arrangements 10" and 10'" could be installed in the recirculation line 24 downstream of the recirculation pump 22 and upstream of the mixer 16 or installed in the downstream transfer line 29 downstream of the transfer pump 28 and downstream of where the displacement line 34 feeds into the upstream transfer line 26.

Figure 5:
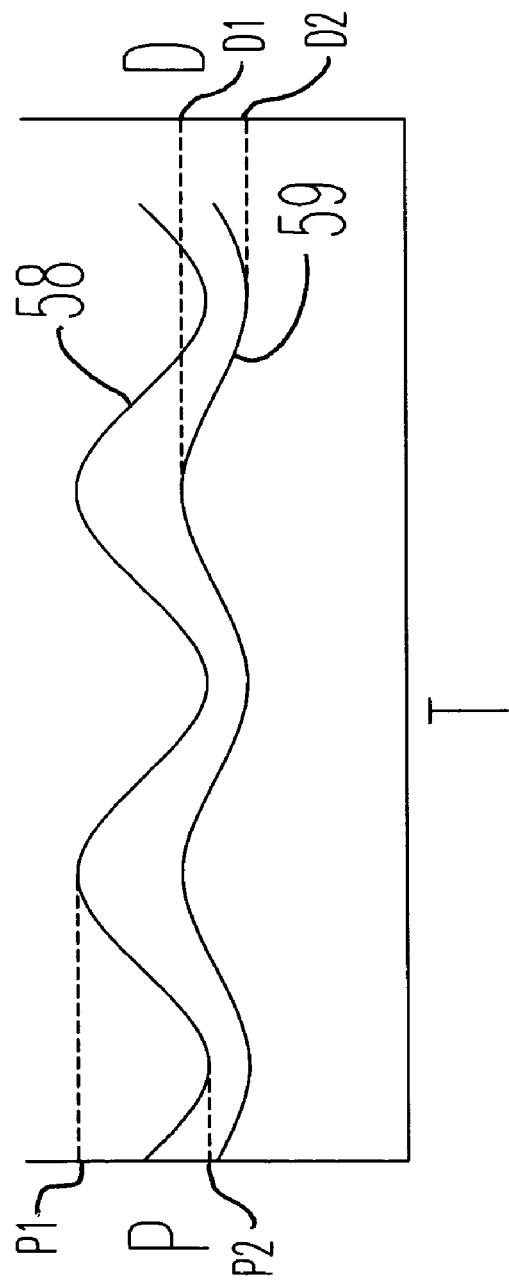
FIG. 5 is a diagram showing the sinusoidal pressure curve and associated density curve generated over time by the third and fourth equipment arrangements.

The third equipment arrangement 10" continuously changes the pressure from a maximum pressure P1 to a minimum pressure P2 within the second alternate densitometer 36A by use of a downstream manifold 54 with one manifold valve 56. The manifold valve 56 would be opened and closed such that a sinusoidal pressure curve 58 would be generated in the densitometer, such as that illustrated in FIG. 5. FIG. 5 is chart showing a typical pressure curve 58 produced when pressure is plotted along a vertical axis and time is plotted along a horizontal axis. The letter "P" on the chart of FIG. 5 represents pressure, the letter "T" represents time, and the letter "D" represents density. The manifold 54 would have a manifold bypass line 60 that would still pass fluid when the manifold valve 54 is closed but at a reduced rate. This would be a more flow restricted situation and thus would cause the second alternate densitometer 36A to operate at a higher pressure. When the manifold valve 56 is open, the flow downstream restriction would be less and therefore the pressure would drop from P1 to P2. If the fluid had air entrainment, then the indicated density would drop from D1 to D2 and the density D2 for the low pressure part of the flow cycle would be recorded.

Figure 6:
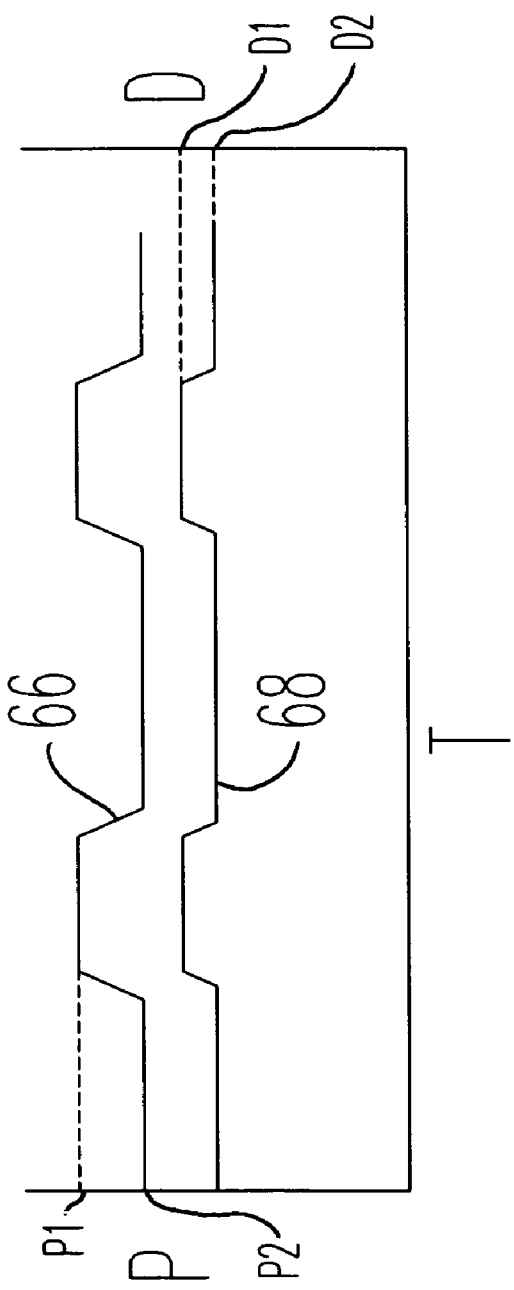
FIG. 6 is a diagram showing the step up-step down pressure curve and associated step up-step down density curve generated over time by the third equipment arrangements where the equipment is operated at an elevated pressure before the pressure is lowered for a period of time before once again resuming operation at the elevated pressure.

Alternately, the third equipment arrangement 10" can be operated in a step up-step down manner to produce the step up-step down pressure curve 66 and associated step up-step down density curve 68 illustrated in FIG. 6. The letter "P" on the chart of FIG. 6 represents pressure, the letter "T" represents time, and the letter "D" represents density. In this type of operation, the step up-step down pressure curve 66 and associated step up-step down density curve 68 are generated over time by operating the third equipment arrangement 10" at an elevated pressure P1, then temporarily lowering the pressure to P2 for a period of time before once again resuming operation at the elevated pressure P1.

The fourth equipment arrangement continuously changes the flow through the third alternate densitometer 36B by using a pulsing, non-centrifugal pump 28P for supplying the flow to the third alternate densitometer 36B, thus changing the pressure within the alternate densitometer 36B. One type of pulsing pump 28P would be an air diaphragm pump. Regardless of whether the third or the fourth equipment arrangements 10" and 10'" is employed to cause the pressure cycle, the corresponding densities D1 and D2 would be measured at the maximum and minimum pressures P1 and P2 during the cycle. Thus, the system could develop density measurements D1 and D2 at two different pressures P1 and P2 and an absolute density Dabs could be calculated using these maximum and minimum values for density and pressure D1, D2, P1 and P2.

This is a very dynamic condition and requires the system measurement devices densitometers 36A and 36B and pressure transducers 40A and 40B to have a fast response time to accurately catch the changing measurements. Micro Motion type Coriolis densitometers have a fast response time and typical pressure transducers will have no problem tracking the changing pressures. The computer system 54, typically employing Allen-Bradley ladder logic computers or laptop computers with signal processors, can process, record and make the required calculations in a timely manner. This arrangement will be more economical because it requires only one densitometer 36A or 36B but some applications may not desire the pulsating pressure in the system. In addition, if the product being measured was inconsistent and varying significantly, this pulsating method may not be appropriate. In the oil well cement mixing process, the slurry is fairly consistent, and therefore, this method could be used in that type of application.

With each of these four different types of equipment arrangements 10, 10' 10" and 10'", there are conditions when one or more of the measurements of the densitometers 36, 36', 36A, 36B, 38 or 38' may not be valid or that slurry density is no longer important due the job stage moving to the displacement mode. In the displacement mode, a cement shut off valve 62 provided in the downstream transfer line 26 is closed to stop flow of cement slurry to the downhole pump 30 and appropriate displacement valves 64A, 64B and 64C provided in the displacement line 34 are opened to allow displacement fluid to flow from the displacement tanks 32A and 32B to the downhole pump 30. In those situations when one of the two densitometers 36, 36', 38 or 38' is no longer providing a valid measurement or is not being used, then the system should be using only the remaining valid densitometer 38, 38', 36 or 36' and thus an absolute density determination Dabs is no longer possible.

For the first equipment arrangement 10, when flow through the second densitometer 38 which is located at the transfer pump 28 falls below a predetermined minimum value, that second or transfer densitometer 38 is no longer providing a valid measurement and the density measurement D2 from that transfer densitometer 38 should be disregarded.

Also, for the first equipment arrangement 10, when there are indications that one or both of the densitometers 36 and 38 is internally blocked due to rocks, thick cement etc, those densitometers 36 and 38 are no longer providing valid measurements and the density measurements D1 and D2 from those densitometers 36 and 38 should be disregarded. If there is an indication of blockage, an output warning should be given to the operator that there is blockage. If only one densitometer 36 or 38 is discredited, then there will need to be a warning that indicates that absolute density Dabs is no longer being calculated. If both densitometers 36 and 38 are discredited, there will need to be a warning that indicates density readings are probably in error and should not be trusted. This can be done with a single density display that can be displayed in different colors. For example, a green density display would indicate that a valid absolute density Dabs is being calculated; a yellow density display would indicate that only one density measurement, D1 or D2, has been determined to be valid; and a red density display would indicate that both densitometers, D1 and D2, are discredited or suspect.

Additionally, for the first equipment arrangement 10, when the system is in a displacement mode, the density measurement D1 from the first or recirculation densitometer 36 should be disregarded. The displacement mode occurs after the slurry mixing process has completed and another fluid is being pumped down hole. In this mode, density measurement with only the second densitometer 38 should be valid since the displacement fluid usually does not have air entrainment problems nor is the density of the displacement fluid as critical. Typical displacement fluids would be water, acid or drilling mud.

The design for the second equipment arrangement 10' ensures that the flow rate through the first alternate first densitometer 36' will be the same as for the first alternate second densitometer 38'. Thus, the only thing that must be maintained is a minimum flow such that a measurable pressure drop is created in the two densitometers 36' and 38'. Assuming that this series arrangement of densitometers 36' and 38' is placed in the recirculation line 24 to the cement slurry mixer 16, then the minimum flow question should not be a problem since the flow is normally constant and of a significant velocity. If the series arrangement is placed in the downstream transfer line 29 going to the high pressure downhole pump 30, this may be a problem since this flow rate can vary from job to job and also during a job. And it would be particularly hard to maintain a minimum flow through the two densitometers 36' and 38' during a squeeze type job.

When employing the second equipment arrangement 10' where the fluid is changing in density or is not quite homogeneous and the flow rate is relatively low, a more accurate absolute density Dabs can be obtained by holding the first densitometer reading D1 in storage for a period equal to the time that it takes the fluid to pass from one densitometer 36' to the other 38'. Thus, the absolute density calculation Dabs would be made from the stored density value D1 from the first densitometer which was stored by the computer system 52 for the time it takes for the sample to get from the first densitometer 36' to the other densitometer 38' and with the real time density value D2 of the second densitometer 38'. In other words, the absolute density Dabs would be calculated from the data from each densitometer 36' and 38' for exactly the same fluid sample as it passed through the two densitometers 36' and 38' in series. In most cases, this will not be necessary since the fluid is somewhat homogeneous.

The third and fourth equipment arrangements 10" and 10'" that each employ only a single densitometer 36A and 36B with cycling pressures, the individual peak pressure P1 and corresponding density D1 and the minimum pressure P2 with the corresponding density D2 could be captured and used to calculate the absolute density Dabs. However, alternately, it should be satisfactory to also capture a running average of the maximum and minimum values P1, D1, P2 and P2 and use these to calculate the absolute density Dabs as this would probably be a more stable measurement.

In addition to the cost advantage of using only one densitometer 36A or 36B for the third and fourth equipment arrangements 10" and 10'", as long as sufficient flow is being passed through the single densitometer 36A or 36B, this arrangement does not need the logic associated with determining the validity of the absolute density Dabs due to one of the two densitometers not having a valid measurement.

Although the present invention has been described in relationship to cement slurry for cementing a gas or oil well, the invention is not so limited and the process can be used for other liquids having entrained gas.

While the invention has been described with a certain degree of particularity, it is manifest that many changes may be made in the details of construction and the arrangement of components without departing from the spirit and scope of this disclosure. It is understood that the invention is not limited to the embodiments set forth herein for the purposes of exemplification, but is to be limited only by the scope of the attached claim or claims, including the full range of equivalency to which each element thereof is entitled.

What is claimed is:

1. A method for determining the absolute density of a liquid or slurry that contains entrained air comprising the following:
    measuring a first density of a liquid or slurry at a first pressure,
    measuring a second density of the liquid or slurry at a second pressure which is different from the first pressure,
    calculating absolute density of the liquid or slurry employing the following derived formula that incorporates the polytropic process model of compressibility of gas:
    absolute density of the liquid or slurry=first density/ $(1-((\text{first density}/\text{second density}-1)/((\text{first pressure}/\text{second pressure})^{1/\text{exponent for pressure-volume polytropic process relationship}}-1)))$,
    wherein first and second densities are continuosly measured by one or more densitometers and first and second pressures are continuously measured by one or more pressure transducers.

2. A method for determining the absolute density of a liquid or slurry that contains entrained air according to claim 1 wherein the density measurement and pressure measurements are constantly transmitted to a computer system that continuously calculates the absolute density of the liquid or slurry in real time.

3. A method for determining the absolute density of a liquid slurry that contains entrained air according to claim 2 wherein the first density and the first pressure are measured in a recirculation line of a cement mixing system by a first densitometer and a first pressure transducer and the second density and second pressure are measured in a transfer line of the cement mixing system by a second densitometer and a second pressure transducer.

4. A method for determining the absolute density of a liquid or slurry that contains entrained air according to claim 2 wherein the first density and the first pressure are measured in liquid or slurry line of a cement mixing system by a first densitometer and a first pressure transducer and the second density and second pressure are measured in the same liquid or slurry line downstream of the first densitometer by a second densitometer and a second pressure transducer that are provided in series with the first densitometer and first pressure transducer.

5. A method for determining the absolute density of a liquid or slurry that contains entrained air according to claim 4 wherein the liquid or slurry line where the densitometers and pressure transducers are measuring the liquid or slurry is the recirculation line.

6. A method for determining the absolute density of a liquid or slurry that contains entrained air according to claim 4 wherein the liquid or slurry line where the densitometers and pressure transducers are measuring the liquid or slurry is the transfer line.

7. A method for determining the absolute density of a liquid or slurry that contains entrained air according to claim 2 wherein both the first density and second density are measured in a liquid or slurry line of a cement mixing system by a first densitometer and wherein both the first pressure and second pressure are measured in the liquid or slurry line by a first pressure transducer.

8. A method for determining the absolute density of a liquid or slurry that contains entrained air according to claim 7 further comprising:
    varying the pressure in the liquid or slurry line between the time of measurement of the first density and the time of measurement of the second density.

9. A method for determining the absolute density of a liquid or slurry that contains entrained air according to claim 8 wherein the pressure in the liquid or slurry line is varied by employing a pulsing pump.

10. A method for determining the absolute density of a liquid or slurry that contains entrained air according to claim 8 wherein the pressure in the liquid or slurry line is varied by employing a varying downstream flow restriction.

11. A method for determining the absolute density of a liquid or slurry that contains entrained air according to claim 2 wherein the pressure and density measurements are taken in a liquid or slurry transfer line.

12. A method for determining the absolute density of liquid or slurry that contains entrained air according to claim 11 wherein the pressure in the liquid or slurry transfer line is varied by employing a downstream manifold with a manifold valve that repetitiously opens and closes to provide a varying downstream flow restriction and varying upstream back pressure.

13. A method for determining the absolute density of liquid or slurry that contains entrained air according to claim 2 wherein the pressure and density measurements are taken in a liquid or slurry recirculation line.

14. A method for determining the absolute density of liquid or slurry that contains entrained air according to claim 13 wherein the pressure in the liquid or slurry recirculation line is varied by employing a downstream manifold with a manifold valve that repetitiously opens and closes to provide a varying downstream flow restriction and varying upstream back pressure.

15. A method for determining the absolute density of liquid or slurry that contains entrained air according under isothermal conditions comprising the following:

measuring a first density of a liquid or slurry at a first pressure, measuring a second density of the liquid or slurry at a second pressure which is different from the first pressure, and calculating absolute density of the liquid or slurry employing the following derived formula that incorporates the isothermal process model of compressibility of gas:

absolute density of the liquid or slurry=first density/
(1−((first density/second density −1)/ (first pressure/second pressure−1))), wherein first and second densities are continuously measured by one or more densitometers and first and second pressures are continuously measured by one or more pressure transducers, wherein the density measurement and pressure measurements are constantly transmitted to a computer system that continuously calculates the absolute density of the liquid or slurry in real time, and wherein the first density and the first pressure are measured in a recirculation line of a cement mixing system by a first densitometer and a first pressure transducer and the second density and second pressure are measured in a transfer line of the cement mixing system by a second densitometer and a second pressure transducer.

16. A method for determining the absolute density of liquid or slurry that contains entrained air under isothermal conditions comprising the following:

measuring a first density of a liquid or slurry at a first pressure, measuring a second density of the liquid or slurry at a second pressure which is different from the first pressure, and calculating absolute density of the liquid or slurry employing the following derived formula that incorporates the isothermal process model of compressibility of gas:

absolute density of the liquid or slurry=first density/
(1−((first density/second density −1)/ (first pressure/second pressure−1))), wherein first and second densities are continuously measured by one or more densitometers and first and second pressures are continuously measured by one or more pressure transducers, wherein the density measurement and pressure measurements are constantly transmitted to a computer system that continuously calculates the absolute density of the liquid or slurry in real time, wherein both the first density and second density are measured in a liquid or slurry line of a cement mixing system by a first densitometer and wherein both the first pressure and second pressure are measured in the liquid or slurry line by a first pressure transducer, varying the pressure in the liquid or slurry line between the time of measurement of the first density and the time of measurement of the second density, and wherein the pressure in the liquid or slurry line is varied by employing a pulsing pump.

* * * * *